United States Patent [19]

Durlacher et al.

[11] Patent Number: 5,261,915
[45] Date of Patent: Nov. 16, 1993

[54] FEMUR BONE RASP WITH ADJUSTABLE HANDLE

[75] Inventors: James M. Durlacher, Indianapolis, Ind.; Scott M. Durlacher, 6963 Oak La., Indianapolis, Ind. 46220

[73] Assignee: Scott M. Durlacher, Indianapolis, Ind.

[21] Appl. No.: 869,769

[22] Filed: Apr. 16, 1992

[51] Int. Cl.⁵ .............................................. A61B 17/32
[52] U.S. Cl. ..................................... 606/85; 606/79; 606/53
[58] Field of Search ................... 606/53, 79, 80, 82, 606/84, 85; 623/23; 403/92, 93, 91, 161, 315, 319

[56] References Cited

U.S. PATENT DOCUMENTS

| | | | |
|---|---|---|---|
| D. 272,648 | 2/1984 | Bolesky et al. | D24/28 |
| D. 273,806 | 5/1984 | Bolesky et al. | D24/28 |
| 435,647 | 9/1890 | Hohenstein | 403/91 X |
| 1,032,898 | 7/1912 | Hane | 403/91 X |
| 1,210,100 | 12/1916 | Pottorf | 403/91 X |
| 1,871,146 | 8/1932 | Bosler | 403/91 X |
| 2,052,331 | 8/1936 | White | 403/93 X |
| 3,815,599 | 6/1974 | Deyerle | 606/85 |
| 4,306,550 | 12/1981 | Forte | 606/85 |
| 4,552,136 | 11/1985 | Kenna | 606/80 X |
| 4,583,270 | 4/1986 | Kenna | 606/85 X |
| 4,587,964 | 5/1986 | Walker et al. | 606/85 |
| 4,601,289 | 7/1986 | Chiarizzio et al. | 606/85 |
| 4,671,275 | 6/1987 | Deyerle | 623/23 |
| 4,739,750 | 4/1988 | Masse et al. | 606/85 |
| 4,765,328 | 8/1988 | Keller et al. | 623/23 X |
| 4,919,679 | 4/1990 | Averill et al. | 623/23 |
| 4,921,493 | 5/1990 | Webb, Jr. et al. | 606/85 |
| 4,990,149 | 2/1991 | Fallin | 606/85 |

FOREIGN PATENT DOCUMENTS

2547192 12/1984 France .

Primary Examiner—Robert A. Hafer
Assistant Examiner—Brian E. Hanlon
Attorney, Agent, or Firm—Woodard, Emhardt, Naughton, Moriarty & McNett

[57] ABSTRACT

A bone rasp for preparing the medullary canal of the femur includes a rasp blade portion shaped and tapered so as to conform to the medullary canal and a handle portion which is designed to be manually attached to the rasp blade and detached from the rasp blade for sterilizing and storing. The handle portion is arranged into two components which are pivotally connected and pinned together. The stationary portion of the handle attaches directly to the rasp blade and the movable or adjustable portion is pinned to the stationary portion at a pivoting location and secured in a selected orientation by a second pin. A series of seven oblong slots are disposed in the stationary portion and arranged on 7½° intervals so as to give the adjustable portion of the handle an approximate 45° range of adjustment. The adjustable handle portion is configured with the stationary portion such that the lower end of the adjustable handle portion contacts and pivots directly against a concave surface so that all mallet forces directed to the adjustable handle portion are transmitted to the stationary portion and not to either the pivot pin or the securing pin.

1 Claim, 5 Drawing Sheets

FEMUR BONE RASP WITH ADJUSTABLE HANDLE

BACKGROUND OF THE INVENTION

The present invention relates in general to orthopedic implements and in particular to rasps for preparing the medullary canal of a bone for receiving a prosthesis implant. More specifically, the present invention relates to the design of an adjustable handle for a femur bone rasp.

Prior to the implant of a prosthesis which is designed to be inserted into the top of the femur and seat within the medullary canal, such as when performing a total hip replacement, the orthopedic surgeon must prepare the medullary canal for the prosthesis. Preparation of the femur canal for receiving the implant involves the use of a bone rasp with a blade portion whose shape is similar to the shape of the prosthesis portion inserted into the femur. The bone rasp also includes a detachable handle and although the rasp handle may be fixed to the blade as an intergral unit, it is more likely and preferred for the handle to be removable by means of a manually releaseable mechanical attachment.

The detachable rasp handle typically extends well above the end or head of the rasp blade and the enlarged head of the handle is normally struck by the orthopedic surgeon by means of a mallet. The striking force is significant but is necessary in order to clean out the medullary canal and shape it correctly for receipt of the prosthesis. It is common for the rasp to be designed for the specific patient taking into consideration the size, shape and orientation of the femur as well as related anatomical aspects.

Typically the rasp blade has a body portion which is of relatively uniform width in a first longitudinal geometric plane and is tapered in the other or second longitudinal geometric plane which is normal to the first plane. In this second geometric plane, the body portion of the rasp blade extends in a proximal direction relative to the femur, bending at an angle of between 40 and 60 degrees as it extends into and terminates in the head of the rasp blade portion. The head has an angled surface in this second geometric plane against which the rasp handle seats. By means of a sliding and interlocking fit the handle is secured to the head of the rasp blade. The handle typically includes an attaching portion and at a fixed angle of incline relative thereto in this first geometric plane, a handle shaft portion. The angles of incline of the blade portion and handle portion in this second geometric plane are such the longitudinal axis of the rasp blade is substantially parallel with the longitudinal axis of the handle shaft portion. Consequently, when the rasp blade is oriented in a substantially vertical fashion, the handle shaft will be substantially vertical as well.

Conventionally, it is preferred to have the handle shaft in a substantially vertical orientation so that the striking action of the mallet by the orthopedic surgeon will not glance off or introduce undesirable angled force vectors. It is desired for the rasp blade and handle shaft to be coplanar in the first geometric plane which is substantially normal to the second geometric plane referenced above.

While the coplanar configuration can generally be achieved independent of the specific femur size, shape and orientation, it is not always possible to achieve a vertical orientation for the handle shaft in the second geometric plane as referred to above. Whenever the anatomy of the femur causes the rasp blade portion to be inserted at an angle off of vertical, such as in order to clear the cut head of the femur, what results is an orientation of the handle shaft at an angle off of vertical. This angle may be either plus or minus (clockwise or counterclockwise) relative to vertical and may be as much as 15 to 20 degrees in either direction. Since the amount of shift off of vertical for each patient can be predetermined by means of x-rays, it is possible to make each femur bone rasp a custom made design in order to keep the handle shaft on the vertical axis even when the anatomy of the femur canal is off of vertical. The custom making of a rasp for each patient is a relatively expensive option and requires more lead time for design and custom manufacturing before the prosthesis can be implanted.

If the rasp handle can be made adjustable relative to the rasp blade then a somewhat standardized rasp blade and handle could be provided and would be suitable for a larger number of patients. As the orientation of the rasp blade relative to the femur shifts from patient to patient, the handle portion would simply be manually pivoted in either a clockwise or counterclockwise direction for the specific patient thereby re-establishing a near vertical orientation for the rasp handle shaft. The present invention is directed to providing such an adjustable rasp handle.

While a variety of rasps and rasp handle designs are known to exist, none of these designs provide the adjustability which is the focus of the present invention. However, consideration of the corresponding patent references may be of interest to appreciate the types of rasp designs which have been conceived of over the years. These patent references include the following:

| Patent Numbers | Patentee | Issue Dates |
| --- | --- | --- |
| 4,739,750 | Masse | 4/26/88 |
| Des. 273,806 | Bolesky | 5/08/84 |
| Des. 272,648 | Bolesky | 2/14/84 |
| 4,306,550 | Forte | 12/22/81 |
| 4,552,136 | Kenna | 11/12/85 |
| 4,919,679 | Averill | 4/24/90 |
| 3,815,599 | Deyerle | 6/11/74 |
| 4,990,149 | Fallin | 2/05/91 |
| 4,601,289 | Chiarizzio | 7/22/86 |
| 4,583,270 | Kenna | 4/22/86 |
| 4,671,275 | Deyerle | 6/09/87 |
| Fr. 2547-192A | France (Lahille) | 5/18/83 |
| 4,765,328 | Keller | 8/23/88 |
| 4,587,964 | Walker | 5/13/86 |

As can be appreciated from a consideration of these various references, they disclose a variety of rasp blade and handle designs many of which are intended for cleaning out and preparing the medullary canal of a bone for the implant of a prosthesis. While some of the references such as Masse disclose adjustability, it discloses adjustability as to the spacing or sizing of the rasp blade portion due to the design of a split blade. Other references such as Bolesky ('806) disclose the offset configuration between the blade portion and the handle portion including the enlarged head which is typically struck by the orthopedic surgeon. This particular design also reveals the detachability between the handle and the rasp blade, in this instance by means of a mechanical attachment. Other references such as the patent to Forte illustrate what might incorrectly be interpreted as a joint of adjustability between the head of the rasp blade and the handle, specifically, item 64 as illustrated in FIG. 1. However, drawings can be misleading and item 64 is simply a transverse slot and does not provide any type of universal connection nor handle adjustability. The device disclosed in Fallin is believed to be typical of the design mentioned regarding the manner of releasing the handle portion from the head of the rasp blade. In this particular design the rasp blade has a generally cylindrical bore into which a pin on the handle is inserted. This pin is spring loaded such that by means of a trigger at the upper end of the handle the pin can be released from the rasp blade in order to separate these two components. As is clear from the design details illustrated and described in the Fallin patent there is no disclosure of nor any means provided for making the connection adjustable.

The lack of any handle adjustability in order to standardize the rasp design for a wider range of patients and still be able to maintain the desired verticality of the handle, is clear from a review of the listed patent references. The French patent in the name of Lahille discloses a hollow rasp with its stem formed by two parts. These two parts are locked into position on the fixed stem portion and thereby create the hollow interior. The focus of this invention, which does not include any handle adjustability, is directed to using the hollow interior for a collection of bone material which is removed from the interior of the femur so as not to clog the teeth of the rasp.

SUMMARY OF THE INVENTION

An orthopedic implement having an adjustable handle according to a typical embodiment of the present invention comprises an implement body member, a handle member which is secured to the implement body member and which includes a stationary base member with a female articulating surface and an adjustable shaft member with a male articulating surface cooperatively disposed against the female articulating surface, the base member being pivotably attached to the shaft member for selective movement of the shaft member relative to the base member to a desired position and means for securing and fixing the shaft member in the selected position relative to the base member.

One object of the present invention is to provide an improved orthopedic implement having an adjustable handle.

Related objects and advantages of the present invention will be apparent from the following descriptions.

BRIEF DESCRIPTION OF THE DRAWINGS

FIGS. 10, 10A, and 10B illustrate in series the manner of connection of the stationary base portion of the rasp handle to the head of the rasp blade portion, wherein FIG. 10A is a section view along line 10A—10A in FIG. 10.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
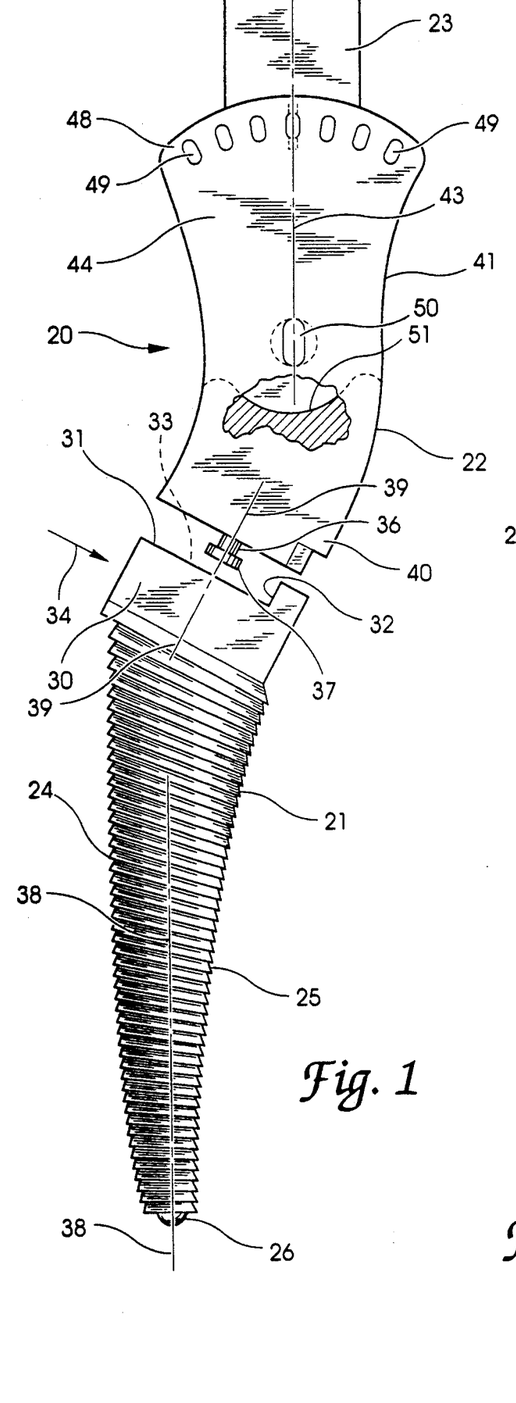
FIG. 1 is a front elevational view of a bone rasp having an adjustable handle.
Figure 2:
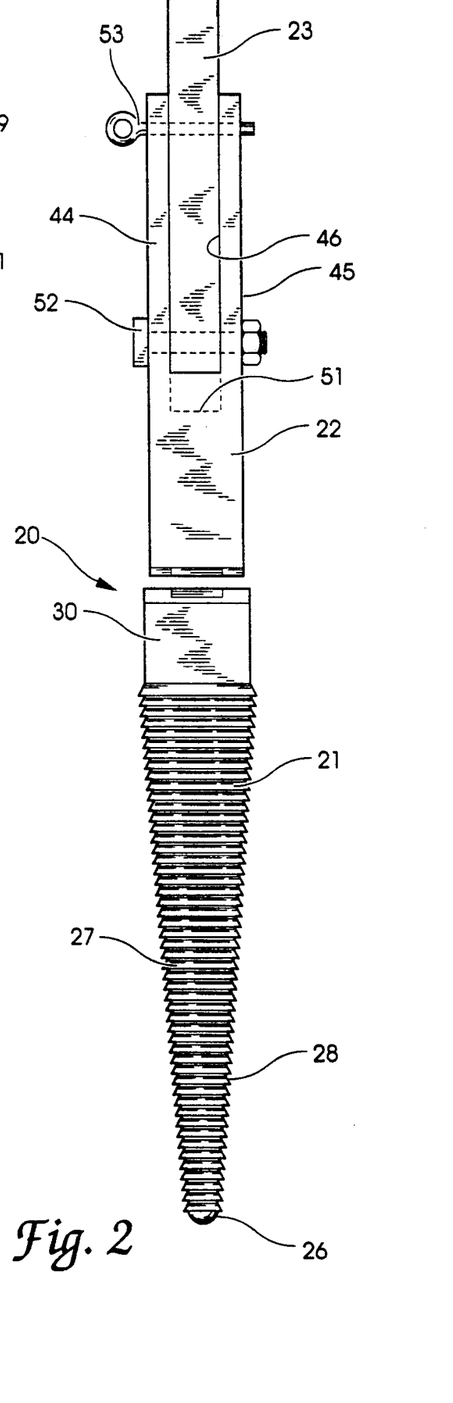
FIG. 2 is a side elevational view of the FIG. 1 bone rasp with adjustable handle.

Referring to FIGS. 1 and 2 there is illustrated an orthopedic bone rasp 20 with an adjustable handle. The three main components of rasp 20 include rasp blade 21, stationary handle portion 22, and adjustable handle portion 23. The focus of the present invention is on the design of an adjustable handle which results from the assembly of the stationary handle portion 22 and the adjustable handle portion 23. Preparation of the medullary canal of a femur for receipt of a prosthesis presents one situation where an adjustable handle will provide an improved design. The importance of an adjustable handle for a femur bone rasp has been outlined in the background discussion regarding this invention.

In the design of rasp 20 the rasp blade 21 has a tapered and angled shape. In one geometric plane, the plane of FIG. 1, the rasp blade surfaces 24 and 25 gradually taper to a rounded tip at 26. There is, as illustrated, a gradual yet smooth curvature at both sides, slightly convex, (side 24) and slightly concave (side 25). In the geometric plane normal to the plane of FIG. 1 (i.e., FIG. 2), surfaces 27 and 28 are substantially straight and converging. However, depending on the shape of the implant, surfaces 27 and 28 may have a very gradual and smooth curvature with both surfaces being slightly concave. Surfaces 24, 25, 27 and 28 are machined with rasp blade cutting edges which are illustrated. If the shape of the prosthesis stem to be implanted is generally rectangular in lateral section that will be the lateral section shape of rasp blade 21. If the prosthesis stem is oval then the edges of blade 21 between surfaces 24 and 25 and 27 and 28 will be rounded or radiused in order to create a compatible oval shape.

The upper portion 30 of the blade is angled and the top surface 31 is fitted with a recessed abutment wall 32 and an undercut keyhole slot 33 (See FIGS. 10, 10A, 10B and 10C). The specific design and assembly procedure of this construction will be discussed in greater detail later. For now, it is enough to understand that the stationary handle portion 22 freely drops down onto surface 31 and then slides to the right in the FIG. 1 orientation, in the direction of arrow 34. Post 36 with an enlarged head 37 drops down into the keyhole slot and slides in the direction of arrow 34 as a locking means. This permits the stationary handle portion to easily assemble to the rasp blade while at the same time precluding separation of the two members by vertical movement. The abutment wall helps to transmit forces through the handle to the rasp blade. The approximate longitudinal centerline of the tapering portion of the rasp blade 21 is denoted by vertical line 38.

Upper portion 30 has a centerline 39 which is normal to top surface 31 and is also the centerline of lower section 40 of stationary handle portion 22. Handle portion 22 is angled roughly midway up which in effect separates the stationary handle portion into an upper section 41 and an integral lower section 40. The angle of bend of handle portion 22 is substantially the same as the angle of bend of rasp blade 21 so that centerline 43 of the upper section 41 is substantially parallel to centerline 38.

Handle portion 22 fits flush against top surface 31 of the rasp blade and is configured as a clevis. The upper section 41 is split into front and rear panels 44 and 45, respectively, which define open channel 46 therebetween. Panels 44 and 45 are shaped and configured in an identical fashion and each includes a flared or diverging top margin 48. The top margin of each panel is arranged with an identical radiating pattern of oblong slots 49. These oblong slots 49 are evenly spaced in a radiating pattern with the radius center located at the geometric center of pivot slot 50. Even though slot 50 is oblong in shape its geometric center is midway between the sides and the ends. The pivot center of slot 50 is fixed regardless of the length of pivot slot 50.

The individual oblong slots 49 also each have a geometric center and these centers are set at the same distance (radius) from the geometric center of pivot slot 50. The center to center spacing is approximately 7½ degrees with a total of one center slot and three side slots equally spaced on either side of the center slot. Movement of the adjustable handle portion relative to the the stationary handle portion is thus made in 7½ degrees increments for a total end to end movement available of 45 degrees. This arrangement of radiating slots 49 and pivot slot 50 are important so that the adjustable handle portion 23 is always able to seat fully on the base 51 of channel 46 even with dimensional and tolerance variations.

Base 51 has a concave curvature (female articulating surface) and the lower surface of handle portion 23 has a matching convex curvature (male articulating surface). This enables the handle portion to smoothly rotate on the base and provide a large surface area of mutual contact. This is important so that forces transmitted through handle portion 23 will pass to the stationary handle portion 22 without any substantial loading either on the pivot pin 52 or on the locking pin 53. These two pins float within slots and these slots are sized so that the pins never bottom out on either end of the slots.

Handle portion 23 extends upwardly and its enlarged head (not illustrated) is designed to be struck by the orthopedic surgeon in order to clean out and prepare the medullary canal of the femur. Although the specific head design for the adjustable portion has not been illustrated, it should be understood that the adjustable handle portion may have generally any length desired and the top end would typically have an enlarged head so as to make striking of that handle easier for the orthopedic surgeon. While the specific head design may vary and while the length of the adjustable handle portion 23 is not critical, it is desired to be able to strike the head in a substantially horizontal plane. This will insure that the full force of the hammer or mallet strike is transmitted vertically through the handle. By avoiding glancing blows and angled force vectors, the preparation of the medullary canal of the femur into the desired size and shape is facilitated.

The orientation of rasp 20 in FIGS. 1 and 2 is in an ideal position with all longitudinal centerlines at or near vertical. This is the orientation when the anatomy of the femur for the particular patient and its orientation relative to the patient permits such a vertical arrangement. However, as the anatomy and orientation of the femur vary from patient to patient, the specific position of the femur and the medullary canal within the femur may shift. This shift is due to specific anatomy differences from patient to patient and it forces centerline 38 to move off of vertical in either a clockwise or counter-clockwise direction. If nothing else changes with regard to the bone rasp, centerline 43 will also shift either left or right of vertical as centerline 38 shifts. In order to re-orient the adjustable handle portion 23 back onto or near a vertical plane, the locking pin 53 is removed from the center slot of the series of oblong slots 49 and the handle portion 23 is rotated about pivot pin 52 in 7½ degree increments. What the orthopedic surgeon is attempting to do is to find another oblong slot 49 which can be used to try and re-establish a near vertical orientation for the adjustable handle portion 23. The oblong slot 49 which has the closest position to vertical is selected and the holes lined up between the stationary and adjustable handle portions and then the locking pin 53 is reinserted.

The adjustability of the handle portion allows the bone rasp to be of a general purpose design in that near verticality of the handle portion can be achieved even when the anatomy of the femur would dictate otherwise. By use of the present invention, a single bone rasp design can be used for a wide range of patients, thus precluding the need for custom-designed femur bone rasps.

Figure 3:
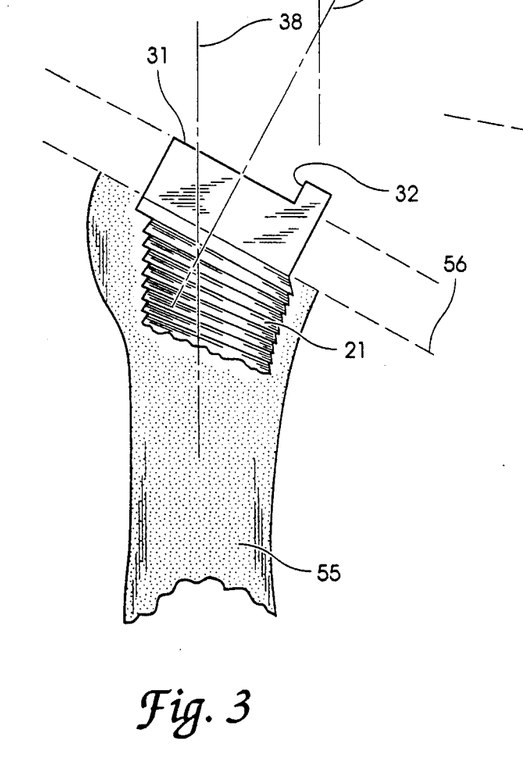
FIG. 3 is a partial front elevational view of the various angles and geometric planes associated with the FIG. 1 bone rasp and the bone being prepared.
Figure 4:
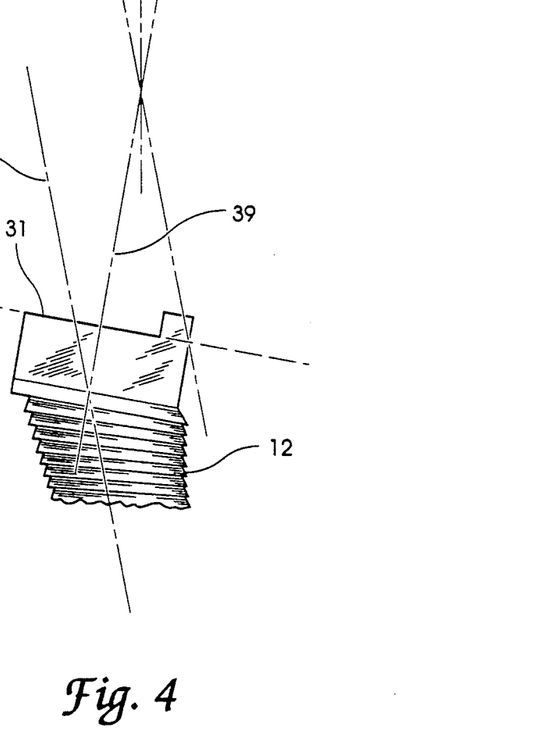
FIG. 4 is a partial front elevational view of various geometric planes of FIG. 3 with the bone rasp in a different orientation.
Figure 5:
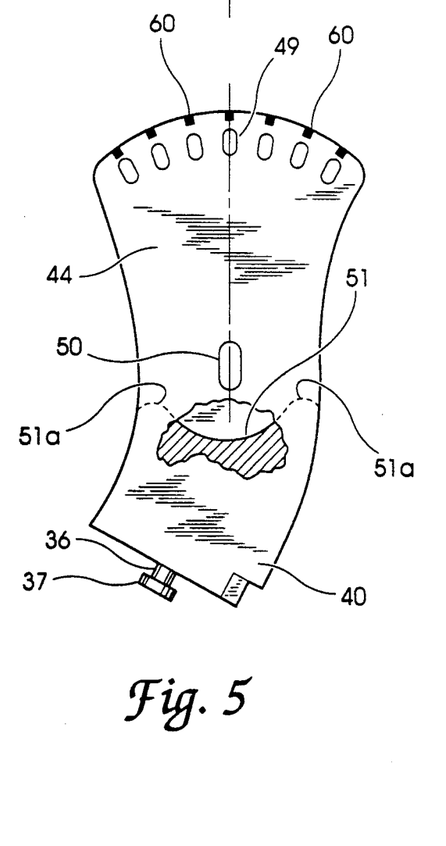
FIG. 5 is a front elevational view of the stationary base portion of the adjustable handle of the FIG. 1 bone rasp.
Figure 5A:
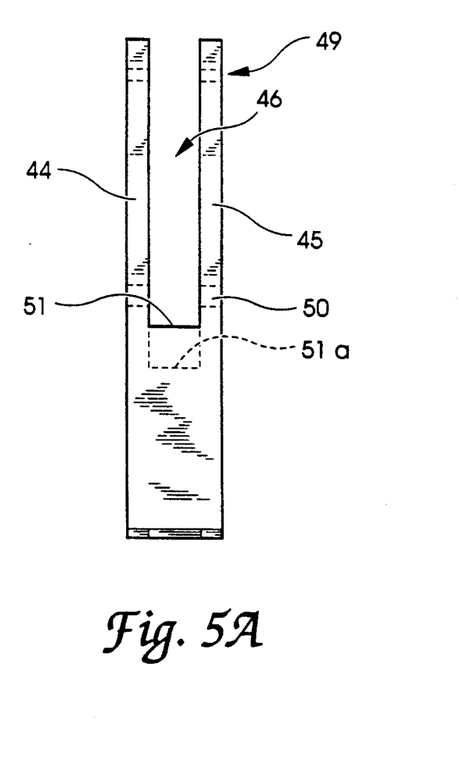
FIG. 5A is a side elevational view of the FIG. 5 stationary base member.

Referring to FIGS. 3 and 4 this centerline geometry which has been described with regard to FIGS. 1 and 2 is illustrated in greater detail. The rasp blade 21 portion of rasp 20 is positioned within the medullary canal of femur 55. Cutting line 56 represents the finished surface of the femur head after preparation for the prosthetic implant. In FIG. 3 the centerlines 38 and 43 are parallel to each other and on vertical. This orientation corresponds to the orientation of FIG. 1. What happens though if due to the anatomy of the femur the medullary canal is shifted off of vertical, such as to the left by roughly fifteen degrees. This is the orientation which is intended to be illustrated in FIG. 4. In this illustration it will be noted that centerlines 38 and 43 are still parallel to each other but are, in fact, shifted off of the vertical plane to the left by roughly 15 degrees. By removing pin 53 handle portion 23 is able to rotated in a clockwise direction back to near vertical which corresponds to line 57. Although the handle portion 23 rotates about pivot pin 52, it is not supported by the pivot pin. Portion 23 is supported by the concave surface of base 51. To guarantee that the pivot pin 52 is not load bearing, the pivot slot 50 is elongated in a vertical direction (see FIGS. 5 and 5A). As might be expected, the geometric center of slot 50 is the radius center for the circular curvature of the base 51. The outer edges 51a of base 51 are broken and radiused in order to avoid the possibility of any interference with the side edges of handle portion 23. The tolerance stack of the dimensions of the component parts may be such that the pivot pin hole 58 in handle portion 23 (See FIGS. 6 and 6A) is not perfectly aligned with the geometric center of slot 50 when the handle portion 23 abuts against base 51. When this occurs, the length of slot 50 provides clearance for a shift off of center in either direction. As such, pivot pin 52 serves more to retain the two handle portions together and the width of slot 50 is just slightly larger than the diameter of pin 52 so as to control any lateral shifting.

Figure 6:
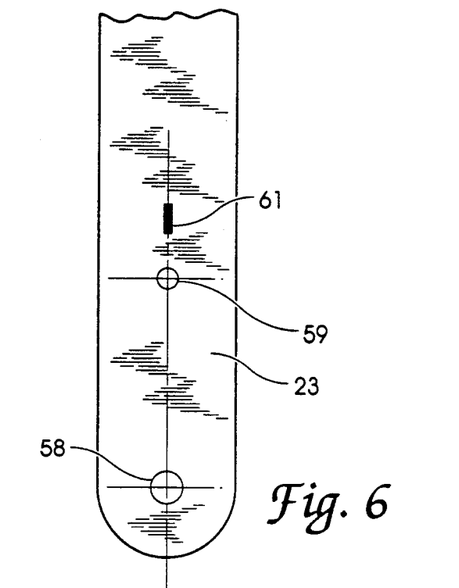
FIG. 6 is a partial front elevational view of the movable handle portion designed for receipt by the FIG. 5 stationary base member.
Figure 6A:
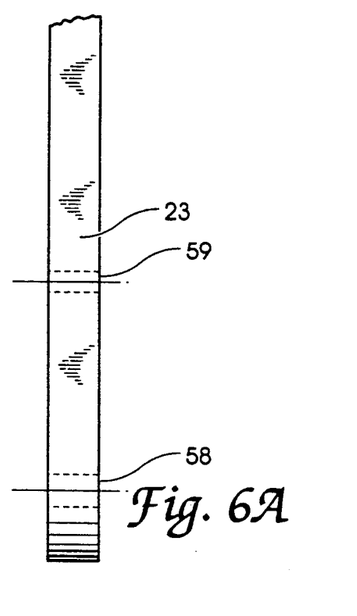
FIG. 6A is a side elevational view in partial form of the FIG. 6 adjustable handle portion.

Adjustable handle portion 23, as illustrated in FIGS. 6 and 6A, includes pivot pin hole 58 and locking pin hole 59. The distance of separation between the centers of these two holes is roughly 1.58 inches which is the radius dimension from the geometric center of slot 50 to the geometric center of each oblong slot 49. Since the width of slot 50 is closely sized to the diameter of the pin 52, any movement of the adjustable handle portion 23 relative to the stationary handle portion 22 will be controlled and guided by the sides of the oblong slot. Consequently, any movement of the locking pin 53 relative to its corresponding oblong slot 49 will be along the same line of travel. Since the oblong slots are oriented with their centerlines on radial lines from the geometric center of slot 50, the slot closest to vertical will be near vertical so that the adjustable portion 23 can move in a near to vertical direction until it abuts against surface 51. This is why the centerlines of the oblong slots 49 are on radial lines. When the adjustable handle portion 23 and stationary handle portion 22 are pinned together, by pin 53, by using the center slot of the pattern of oblong slots 49, centerline 43 is the centerline of handle portion 23. As the stationary handle portion shifts due to the anatomy of the femur, the centerline of the adjustable handle portion can be maintained on centerline 57.

Markings 60 are provided along the top surface and front side of stationary handle portion 22 as a means to facilitate positioning of the adjustable handle portion 23. When it is necessary to reposition the adjustable handle portion, pin 53 is removed, the adjustable handle portion is moved back to near vertical and the locking pin 53 is reinserted. In order for the locking pin to be reinserted, it is necessary to position hole 59 in line with the oblong slot 49 which is closest to vertical (centerline 57). The corresponding mark 61 is provided to located the geometric center of hole 59. The consequence of lining up marking 61 with marking 60 is that the required holes are in alignment and the adjustable handle portion is brought closest to vertical based upon the position of the oblong slots. As hole 59 is brought into registration with the corresponding oblong slot that is closest to vertical, there will be the opportunity to feel when the locking pin 53 can slide in through the pair of holes that are in registration. The locking pin initially inserts through the front panel 44 of the stationary handle portion into the adjustable handle portion 23 and then on through into the back panel 45 of the stationary handle portion 22.

Figure 8:
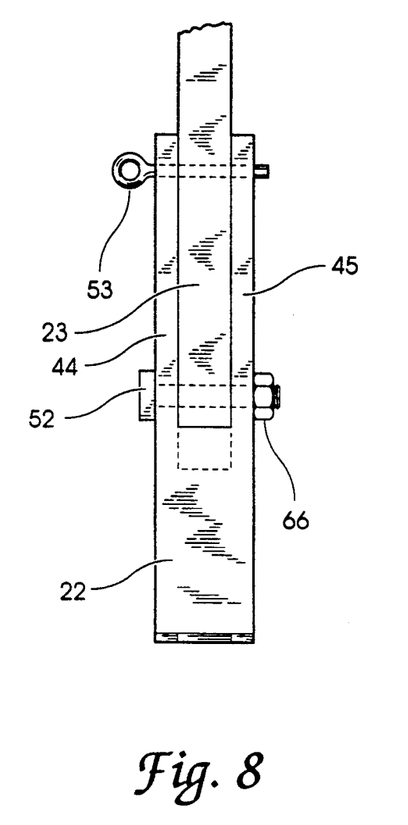
FIG. 8 is a side elevational view of the FIG. 7 assembly detailing the specific pinning numbers.

As noted, the oblong slot patterns in front panel 44 are duplicated on rear panel 45 so that the pinning of the adjustable handle portion 23 by pin 53 is as illustrated, in FIG. 2 and FIG. 8.

Figure 7:
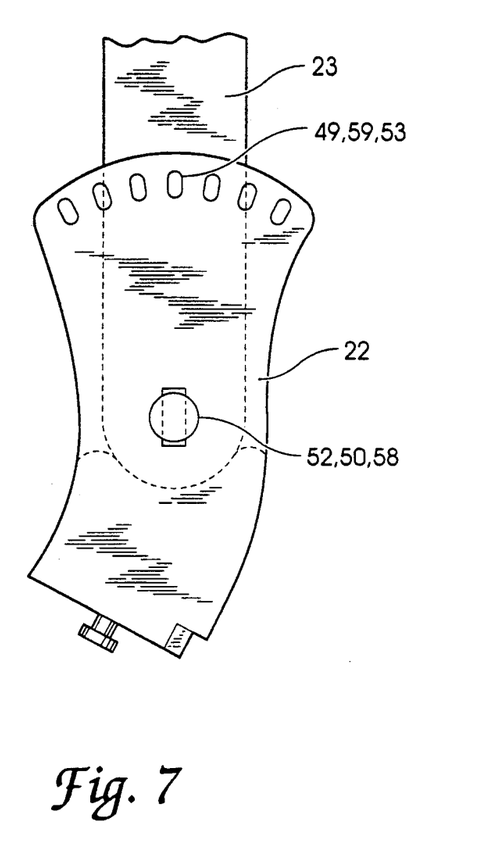
FIG. 7 is a partial front elevational view of the adjustable handle portion illustrating the pinned connections.
Figure 9:
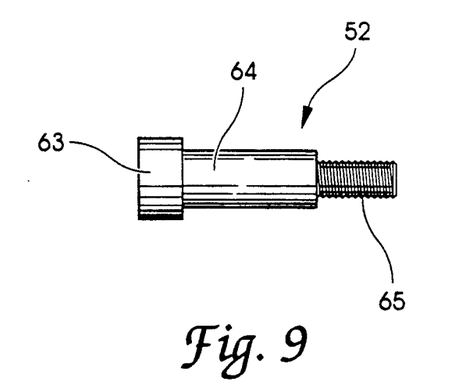
FIG. 9 is a side elevational view of a shouldered bolt used in the assembly of FIGS. 7 and 8.
Figures 10, 10A, 10B:
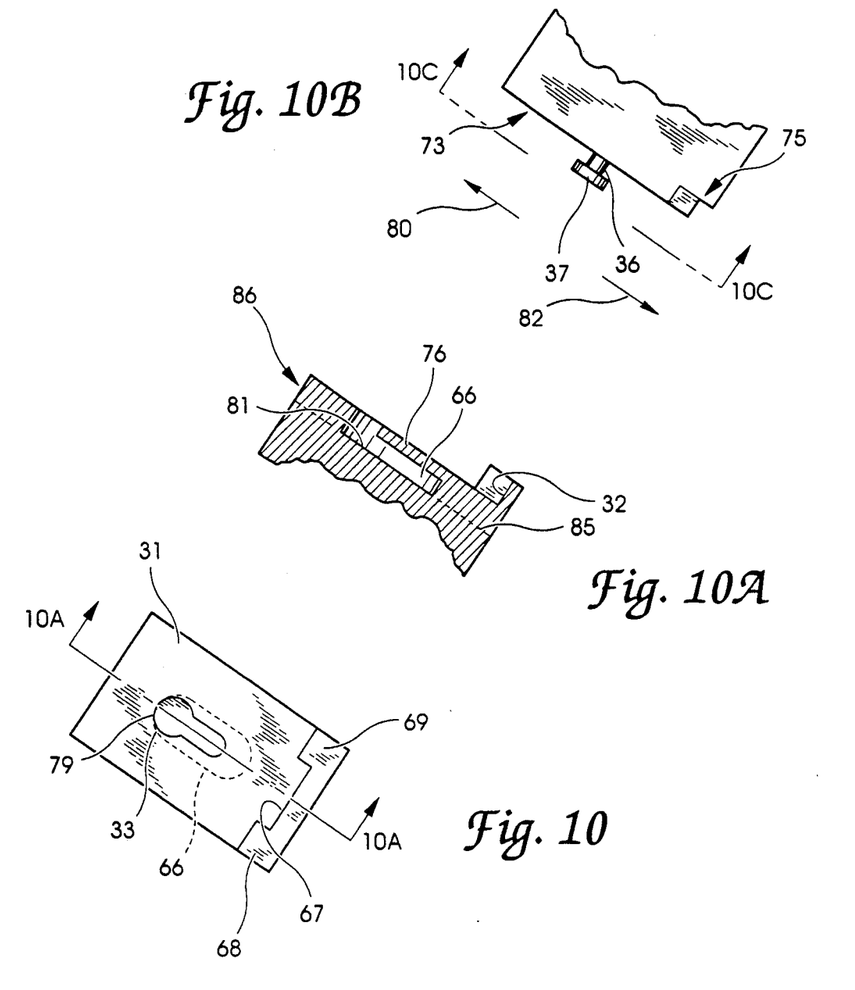
Figure 10C:
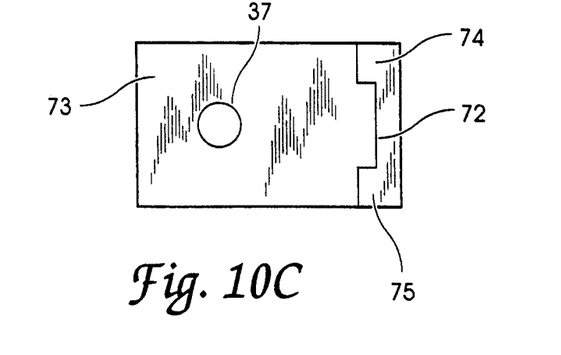
FIG. 10C is a bottom plan view of the stationary base member of the rasp handle as viewed along line 10C—10C in FIG. 10B.

The pinning together of the stationary handling portion 22 and adjustable portion 23 by pins 52 and 53 is illustrated in greater detail in FIGS. 7 and 8. Pin 52 (see FIG. 9) is a shouldered bolt with an enlarged head 63 and a smooth, cylindrical body 64 which terminates in a smaller diameter threaded portion 65. Head 63 may be of hex shape or slotted. The length of the pin body 64 is slightly greater than the maximum width or thickness of stationary handle portion 22. The threaded portion 65 receives a nut 66 which can be tightened fully and when the assembly is completed, pin 52 is free to move axially, but only a very slight distance. Pin 53 is configured as a quick connect/disconnect pin which can be easily inserted and removed, yet it will hold is position when inserted in order to lock the adjustable handle portion into position. It is intended that most of the striking force on the top of the adjustable handle portion 23 will be transferred directly through the adjustable handle portion to the stationary handle portion 22. However, when the adjustable handle portion and stationary handle portion are shifted off of vertical from each other, some angled force vectors may inevitably act on pin 53. However, the size of pin 53 and the appropriate material selection based on tensile strength will preclude any weakening or failure of pin 53 even for these angled force vectors.

Referring to FIGS. 10, 10A, 10B and 10C the interfit between the rasp blade 21 and stationary handle portion 22 is illustrated. Top surface 31 of the upper portion 30 of the rasp blade 21 includes a keyhole slot 33 which opens downwardly into an undercut and open area 66. Abutment wall 32 is configured with symmetrical inset portion 67 centered between side wall portion 68 and 69. The lower section 40 of the stationary handle portion includes an interlocking tab projection 72. The size and shape of top surface 31 is virtually identical to bottom surface 73 as illustrated by FIGS. 1, 2, 10, 10A and 10B.

In this arrangement of rasp blade 21 and stationary handle portion 22, it is to be understood that the size and shape of sidewall portions 68 and 69 are virtually identical to the size and shape of open voids 74 and 75. Similarly, the undercut on stationary handle portion 22 is compatibly sized with the height of abutment wall 32 so that surface 73 can fit flush against surface 31 and make full surface contact without the size and shape of sidewall portions 68 and 69 as well as portion 67 creating any type of interference with the mating portions and surfaces on stationary handle portion 22. As should be understood, the interfit of sidewall portions 68 and 69 into open voids 74 and 75 and the interfit of projection 72 into and up against clearance portion 67 is not the critical fit between the stationary handle portion 22 and the rasp blade. What the interfit of these various surfaces achieve is a controlled fit so that the stationary handle portion will be locked against any lateral movement or shifting. Additionally, any mallet forces directed against the enlarged head of the adjustable handle portion in addition to being transmitted directly through the body of the rasp blade may also apply certain forces against abutment wall 32 and thus the wall serves an important function in the sense of receiving and transmitting forces directly to the rasp blade.

In order to prevent the stationary handle portion 22 from pulling upwardly and separating from rasp blade 21, it is to be understood that the enlarged head 37 is locked beneath shelf 76 within open undercut area 66. While post 36 is roughly centered in bottom surface 73, the enlarged opening 79 of keyhole slot 33 is shifted to the left of center in the direction of arrow 80. Consequently, in order to assemble the stationary handle portion to the rasp blade 21, the stationary handle portion 22 must be shifted in the direction of arrow 80 so that the enlarged head 37 lines up with the enlarged opening 79. Head 37 is then pushed downwardly into the keyhole slot until the enlarged head 37 extends below shelf 76 and enters the undercut clearance area 66. The required initial position is achieved once head 37 abuts up against surface 81. Once this occurs, the stationary handle portion is then shifted to the right in the direction of arrow 82 until projection 72 abuts up against portion 67. In this orientation the enlarged head 37 is locked beneath shelf 76. Any attempt to separate the stationary handle portion from the rasp blade by pulling upwardly causes the enlarged head 37 to abut up against the underside of shelf 76 precluding separation of these two components by vertical motion.

The inclined angle orientation of top surface 31 (See FIG. 1) means that simply the force of gravity will keep the stationary handle portion and the rasp blade together. The rasp blade can be lifted by use of the stationary handle portion and lateral movement is restricted by the positioning of projection 72 between sidewall portions 68 and 69 as well as by the edges of the keyhole slot acting against post 36.

In order to easily create the keyhole slot 33 and open area 66, a cover plate is created and secured to the remainder of the rasp blade. Broken line 85 represents the joined surface interface when a cover plate is used. The cover plate 86 can be secured by threaded fasteners or alternatively by welding. The cover plate 86 is the illustrated portion of rasp blade 21 above line 85.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A bone rasp for preparing the medullary canal of a femur for receipt of a prosthesis, said bone rasp comprising:
   a bone rasp blade member; and
   an adjustable handle detachably assembled to said blade member, said adjustable handle including:
   a stationary base member assembled to said blade member having oppositely-disposed front and rear panels and a concave base surface extending therebetween, said front and rear panels in combination with said base surface defining an interior channel;
   an adjustable handle shaft pivotally secured to said stationary base member for selective positioning of said handle shaft, said handle shaft being disposed within said interior channel and having a convex lower surface disposed against said concave base surface; and
   insertable means for fixing the position of said handle shaft relative to said stationary base member.

* * * * *